United States Patent [19]

Baur et al.

[11] Patent Number: 5,068,416
[45] Date of Patent: Nov. 26, 1991

[54] PREPARATION OF β-ALANINEDIACETIC ACID OR ITS ALKALI METAL OR AMMONIUM SALTS

[75] Inventors: Richard Baur, Mutterstadt; Charalampos Gousetis, Ludwigshafen; Wolfgang Trieselt, Ludwigshafen; Werner Bochnitschek, Ludwigshafen; Alfred Oftring, Bad Durkheim, all of Fed. Rep. of Germany

[73] Assignee: BASF Aktiengesellschaft, Ludwigshafen, Fed. Rep. of Germany

[21] Appl. No.: 394,816

[22] Filed: Aug. 17, 1989

[30] Foreign Application Priority Data

Sep. 2, 1988 [DE] Fed. Rep. of Germany ....... 3829859

[51] Int. Cl.$^5$ .............................................. C07C 229/00
[52] U.S. Cl. ...................................................... 562/571
[58] Field of Search ......................................... 562/571

[56] References Cited

U.S. PATENT DOCUMENTS 3,260,745   7/1966   Andress ................................. 562/571
4,133,929   1/1979   Bowes .................................... 428/280
4,563,478   1/1986   Curti ..................................... 562/571

FOREIGN PATENT DOCUMENTS 265818   5/1988   European Pat. Off. .

OTHER PUBLICATIONS

Allinger, "Organic Chemistry," pp. 524-526 (1971).
Chaberek, J. Am. Chem. Soc., 75, pp. 2888-2892 (1953).
Helv. Chim. Acta 32, (1949), S. 1184, pp. 1174-1187, G. Schwarzenbach et al.
Zh. Vses. Khim. Obschestva im., D.I. Mendeleeva 10, 1965, p. 105, V. G. Yashunskii, et al. (with English Abstract CA 62:16232, 1965).

Primary Examiner—Michael L. Shippen
Attorney, Agent, or Firm—Oblon, Spivak, McClelland, Maier & Neustadt

[57] ABSTRACT

β-Alaninediacetic acid (Ia) or its alkali metal or ammonium salts (Ib) are prepared by a process in which iminodiacetic acid and acrylic acid (a) for the preparation of Ia, are reacted with one another in a nonbasic aqueous medium and
(b) for the preparation of Ib, are reacted with one another in an alkaline aqueous medium or an aqueous medium containing a nitrogen base, or the Ia formed in the nonbasic medium is converted with an alkali metal base, ammonia or an amine into Ib.

3 Claims, No Drawings

PREPARATION OF β-ALANINEDIACETIC ACID OR ITS ALKALI METAL OR AMMONIUM SALTS

The present invention relates to a novel process for the preparation of β-alaninediacetic acid (Ia) or its alkali metal or ammonium salts (Ib).

Like nitrilotriacetic acid or ethylenediaminetetraacetic acid or the salts of these aminopolycarboxylic acids, the compounds Ia and Ib are important complexing agents.

It is known that β-alaninediacetic acid can be prepared by preparing chloroacetic acid with β-alanine (G. Schwarzenbach et al., Helv. Chim. Acta 32 (1949), 1184). The cyanomethylation of β-alanine to β-alaninediacetonitrile (V.G. Yashunskii et al., Zh. Vses. Khim. Obschestva im. D.I. Mendeleeva 10 (1965), 105) and the reaction of iminodiacetic acid with acrylamide to give β-alanine-N,N-diacetic acid monoamide (DE-A 27 27 755) have also been disclosed.

The two first-mentioned processes require β-alanine as a starting material, which is relatively difficult to obtain, and necessitate a plurality of process stages, while the addition reaction of iminodiacetic acid, which is readily obtainable from ammonia, hydrocyanic acid and formaldehyde, with acrylamide, and the cyanomethylation of β-alanine, give only one derivative of β-alaninediacetic acid, from which the acid is obtained only by subsequent hydrolysis of the cyano group or of the amide group.

It is an object of the present invention to make the title compounds Ia and Ib more readily obtainable than in the past.

We have found that this object is achieved by a process for the preparation of β-alaninediacetic acid (Ia) or its alkali metal or ammonium salts (Ib), wherein iminodiacetic acid and acrylic acid a) for the preparation of Ia, are reacted with one another in a nonbasic aqueous medium and b) for the preparation of Ib, are reacted with one another in an alkaline aqueous medium or an aqueous medium containing a nitrogen base, or the Ia formed in the nonbasic medium is converted with an alkali metal base, ammonia or an amine into Ib:

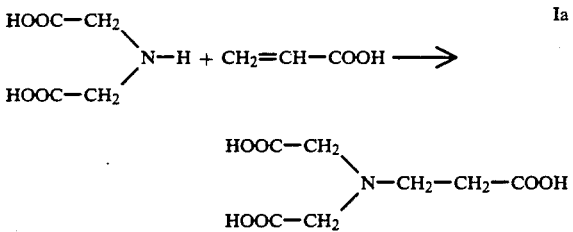

Advantageously, equimolar amounts of acrylic acid and iminodiacetic acid are used. The organic acids are used in an amount of, in general, 20 to 50, preferably from 30 to 40, % by weight, based on the total aqueous mixture. The reaction begins noticeably at 20° C. and usually takes from 2 to 20 hours at from 60° to 100° C..

To achieve a shorter reaction time, the reaction may be carried out at higher temperatures of up to 200° C. in an autoclave.

The temperature range of from 70 to 100° C. is preferred for reasons relating to application. By adding small amounts of organic or inorganic acids, such as formic acid, acetic acid, hydrochloric acid or sulfuric acid, the reaction rate can be increased. Ia is preferably prepared at a pH of from 0 to 1.

When the reaction is complete, the crystalline acid can be isolated from the aqueous solution by a conventional method.

Advantageously, up to 50% of the water are first removed from the reaction mixture under reduced pressure. The residue is then advantageously cooled to 0–5° C., and the β-alaninediacetic acid can be crystallized out, filtered off and washed with ice water in amounts of up to 50% of the amount of water used as a solvent for the reaction of the iminodiacetic acid with acrylic acid. The product is obtained in a purity of from 97 to 99.5% by weight and in yields of from 95 to 98.5%.

Aminopolycarboxylic acids very generally have a low water solubility, and it is for this reason that in many cases their alkali metal or ammonium salts, which are more readily soluble in water, are preferably used.

The corresponding salts of β-alaninediacetic acid (Ib) in which all three acid functions are neutralized are directly obtainable by embodiment (b) when the novel process is carried out in a neutral basic medium, advantageously at a pH of from 7 to 9, and an alkali metal hydroxide, ammonia or an organic amine is added as the neutralizing base.

Sodium hydroxide solution is preferably used, but it is also possible to employ other basic compounds, such as sodium carbonate, sodium bicarbonate, potassium hydroxide, potassium carbonate or ammonia. Other salt-forming bases which may be used are primary, secondary or tertiary aliphatic organic amines where the aliphatic radicals are of 1 to 4 carbon atoms, for example methylamine, dimethylamine or trimethylamine. The other reaction conditions in the case of embodiment (b) are the same as those in procedure (a). The acids Ia can of course also be converted subsequently into their salts Ib in a conventional manner.

The novel process can be carried out both batchwise and continuously and permits the large-scale industrial production of β-alaninediacetic acid or its alkali metal or ammonium salts in a simple manner in high yields and high purity.

EXAMPLE 1

A stirred mixture of 36 g (0.5 mole) of acrylic acid, 66.5 g (0.5 mole) of iminodiacetic acid, 130 ml of water and 20 ml of anhydrous acetic acid was kept at 100° C. for 3 hours.

After the mixture had been cooled to room temperature, 50 ml of water and acetic acid were removed under reduced pressure (0.02 atm). The reaction mixture was then cooled to 5° C., after which the product precipitated in crystalline form was filtered off and washed with 60 ml of ice water.

Yield: 100.5 g (0.49 mole) of β-alaninediacetic acid = 98.5%.

Purity: 99.5% by weight.

EXAMPLE 2

A mixture of 267 g (2.0 moles) of iminodiacetic acid and 500 ml of water was neutralized with 50% strength by weight NaOH to pH 7.

144 g (2.0 moles) of acrylic acid were then added dropwise in the course of 30 minutes while stirring, the pH of the mixture being kept at 7–8 by synchronous addition of 50% strength by weight NaOH. The reaction mixture was then stirred for 12 hours at 70° C.. 250 ml of water were then removed under reduced pressure (0.02 atm). The mixture was then cooled to 0° C., after which the product precipitated in crystalline form was filtered off and washed with 150 ml of ice water.

Yield: 525 g (1.94 moles) of the trisodium salt of β-alaninediacetic acid = 97%.

Purity: 99.2% by weight.

We claim:

1. A process for the preparation of β-alaninediacetic acid comprising:
    reacting iminodiacetic acid and acrylic acid in a non-basic aqueous medium to form said β-alaninediacetic acid.
2. The process of claim 1, wherein said reaction is carried out at from 70 to 100° C.
3. The process of claim 1, wherein said aqueous medium has a pH of from 0 to 1.

* * * * *